United States Patent [19]

Roll et al.

[11] Patent Number: 4,690,486

[45] Date of Patent: Sep. 1, 1987

[54] FOUR POSITION INTERLACING APPARATUS

[75] Inventors: Walter F. Roll, Blue Ridge; Michael Campbell, Dallas, both of Tex.

[73] Assignee: Texas Instruments Incorporated, Dallas, Tex.

[21] Appl. No.: 728,127

[22] Filed: Apr. 29, 1985

[51] Int. Cl.⁴ .............................................. G02B 26/10
[52] U.S. Cl. ...................................... 350/6.6; 350/486
[58] Field of Search ................. 350/6.1, 6.5, 6.6, 486, 350/6.91

[56] References Cited

U.S. PATENT DOCUMENTS 4,488,789 12/1984 Kenney ............... 350/486

FOREIGN PATENT DOCUMENTS 252387 1/1927 United Kingdom ............... 350/6.6

*Primary Examiner*—John K. Corbin
*Assistant Examiner*—Loha Ben
*Attorney, Agent, or Firm*—Richard K. Robinson; James T. Comfort; Melvin Sharp

[57] ABSTRACT

A four position interlacing apparatus includes an interlace mirror of electromagnetic material, and an interlace mirror support member of magnetic material having a faceted surface for supporting the interlace mirror. The supporting surface has a centrally disposed ridge from which a pair of downwardly sloping facets extend at first preselected interlace angles to form ridges with a pair of downwardly sloping facets extending therefrom at second preselected interlace angles, and a corresponding plurality of bars of non-magnetic material for dividing each facet between the ridges to form a plurality of magnetic core members. Each bar of non-magnetic material extending vertically downward to aperture forming walls of the support member, said support member having solid reel bars formed in the apertures with a plurality of coils surrounding the reel bars. A control circuit selectively energizes the coils first in one direction to magnetize the cores in a preselected order to draw the interlace mirror to the energized facet and in an opposite direction to assist in the movement of the interlace mirror to the next selected facet.

7 Claims, 6 Drawing Figures

FOUR POSITION INTERLACING APPARATUS

This invention relates to optical element positioners and more particularly to an infrared device interlace mechanism.

Many processes in industrial, scientific and military applications require accurate placement and positioning of optical elements. Often, a discrete number of predetermined positions are required to be repeatedly accessed at high rates of speed and with substantial accuracy.

The positioning of optical components has been accomplished manually through the use of hand operated micrometers and translation/rotation stages; while automation has been accomplished by the replacement of the micrometer with computer controlled stepper motors, servo/galvanometers or piezoelectric transducers. The computer controlled actuators are capable of high resolution and a large number of positions when coupled with the proper mechanical drive train, but are extremely costly owing to the complexity of their construction and bulky owing to the requirement for a computer controller and a large number of mechanical parts.

Accordingly it is an object of this invention to provide an optics positioning interlace device which is simple in construction, compact in size, fast in operation and low in cost.

Another object of the invention is to provide an optics positioning interlace device capable of providing extremely accurate and rapid positioning of optical components over a small range of angular positions.

Briefly stated, this invention comprises an optical interlacing device which utilizes an electromagnet operable in response to an electrical circuit for positioning an interlace mirror of magnetic material on a faceted surface in the optical path of an infrared detecting device. The faceted surfaces are shaped for accurately positioning the interlace mirror for producing adjacent lines belonging to different fields.

Other objects and features of the invention will become more readily apparent from the following detailed description when read in conjunction with the accompanying drawings in which:

FIG. 1 is a side view of a four position interlacer constituting the subject matter of this invention;

FIGS. 2a 2a' and 2b constitute a circuit diagram for the four position interlacer of FIG. 1;

Figure 1:
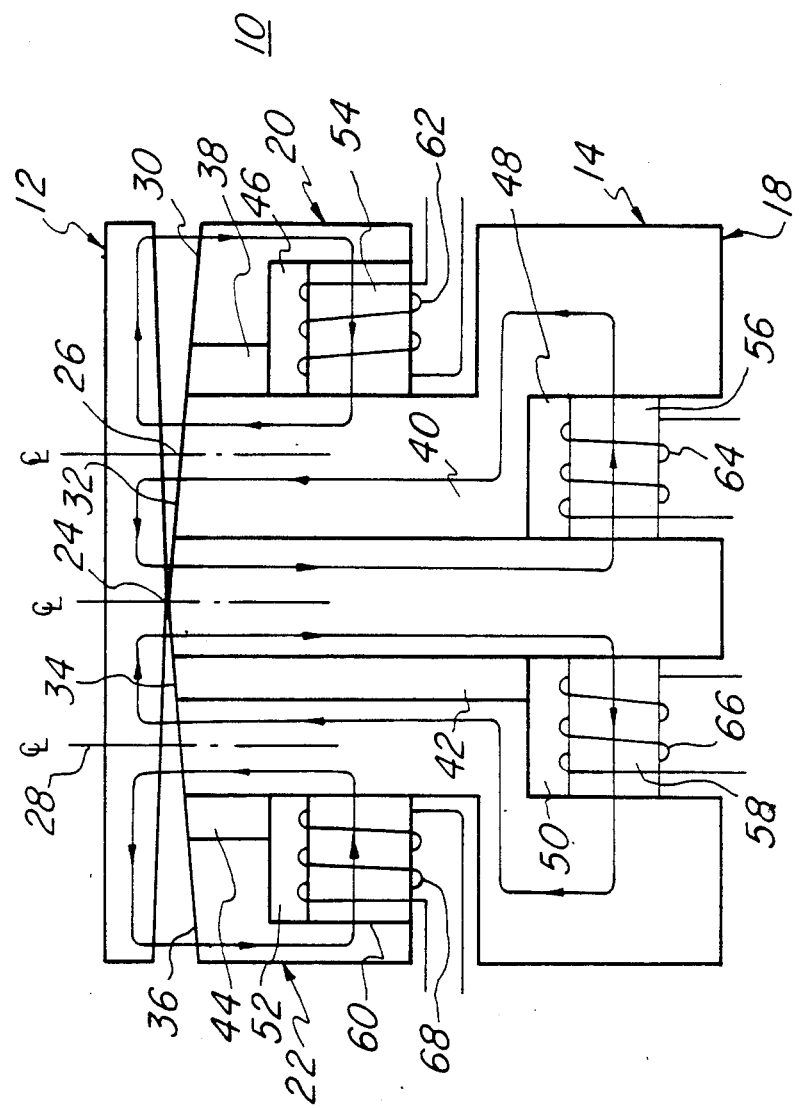

Referring now to FIG. 1, the four position interlacer 10 comprises a reed type interlace mirror of high permeability alloy 12 and a supporting member of magnetic material 14. The read interlace mirror support member 14 includes five blocks of magnetic alloy and four non-magnetic isolation blocks forming top and bottom surfaces 16 and 18, side surfaces 20 and 22 and walls forming passages 38, 40, 42 and 44 to cavities 46, 48, 50 and 52. The cavities 46, 48, 50 and 52 contain solid bar reels 54, 56, 58 and 60.

The top surface 16 has a ridge 24 centrally disposed between the sides 20 and 22, and parallel ridges 26 and 28 on either side of ridge 24 and spaced therefrom. Ridges 24, 26 and 28 define planar surfaces 30, 32, 34 and 36. The surfaces 32 and 34 slope downwardly from ridge 24 to ridges 26 and 28, respectively, to form first and second interlace position angles; while, the surfaces 30 and 36 slope downwardly from ridges 26 and 28 to sides 20 and 22, respectively, to form third and fourth interlace position angles.

The passages 38, 40, 42 and 44 are filled with a non-magnetic material such as brass. Cavity 46 opens at side 20, cavities 48 and 50 open at bottom 18, and cavity 52 opens at side 22 to provide outlets for coils 62, 64, 66 and 68 of conductive (magnet) wire wrapped around the solid bars 54, 56, 58 and 60 respectively.

In this arrangement, when the coils are selectively energized, four separate magnetic flux paths are formed to draw the interlace mirror reed, respectively, to the facets 32, 34, 36 and 30 of top surface 16. It is important to note that as the interlace mirror is drawn to the surfaces the air trapped there between acts to dampen the impact of the interlace mirror with the surfaces. This dampening effect reduces noise, "over shoot" or bounce and increases meantime before failure factor. It will be appreciated by those skilled in the art that the facets control the accuracy of the mirror's operation and that the ridges formed at their intersections are not critical to the operation.

Figure 2A:
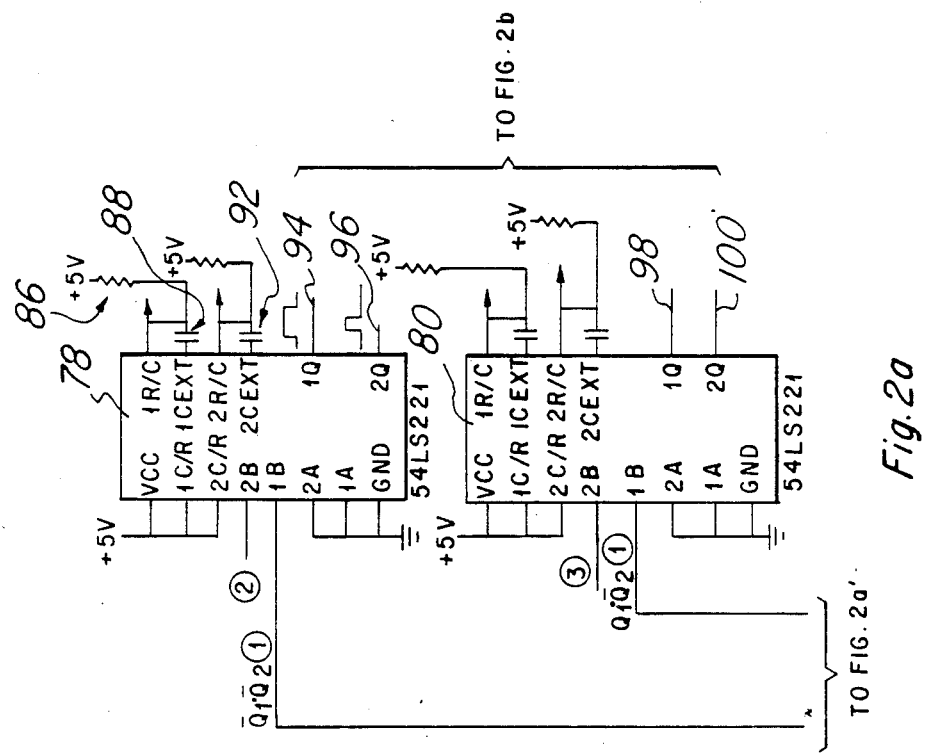
Figure 2A:
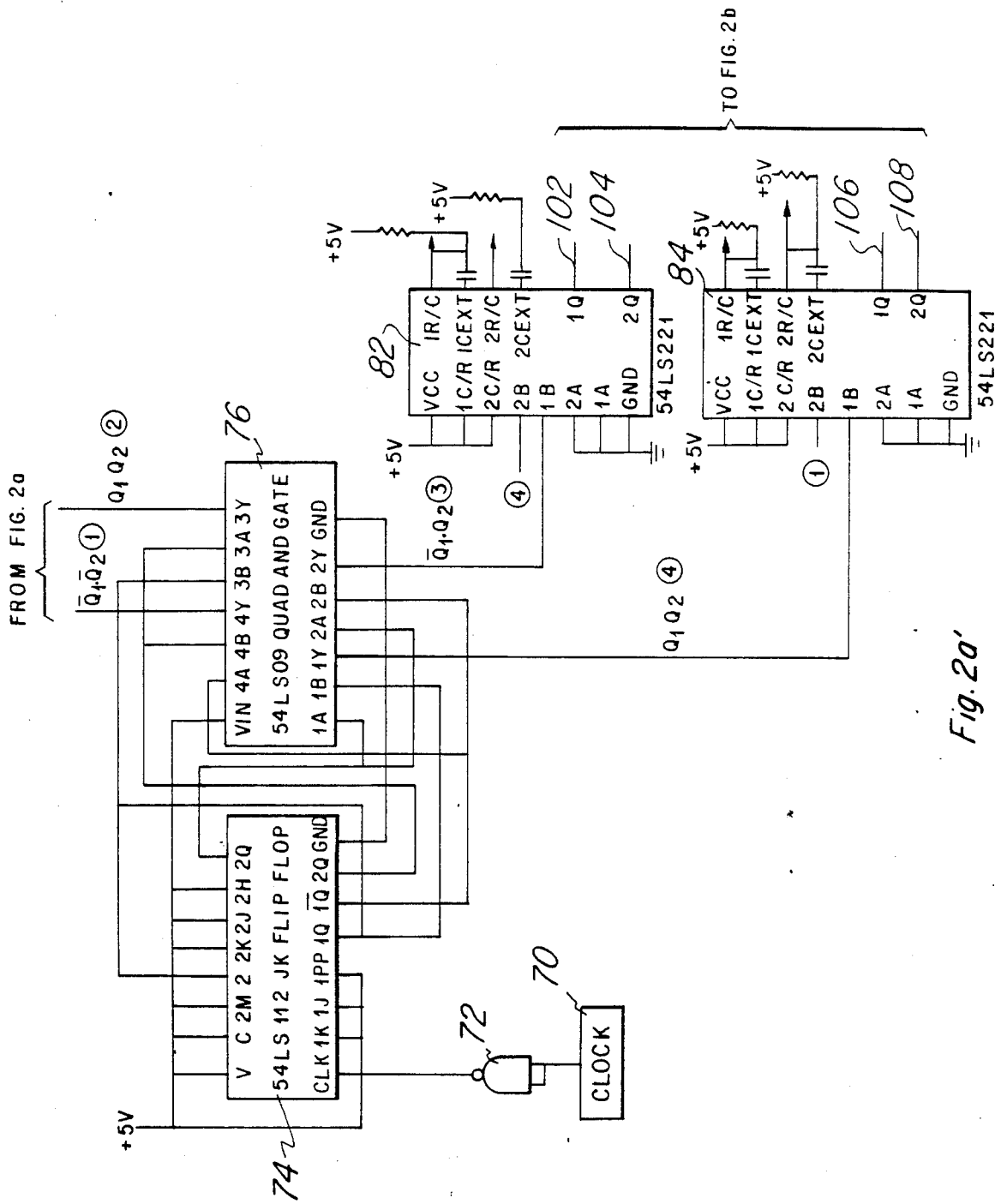
Figure 2B:
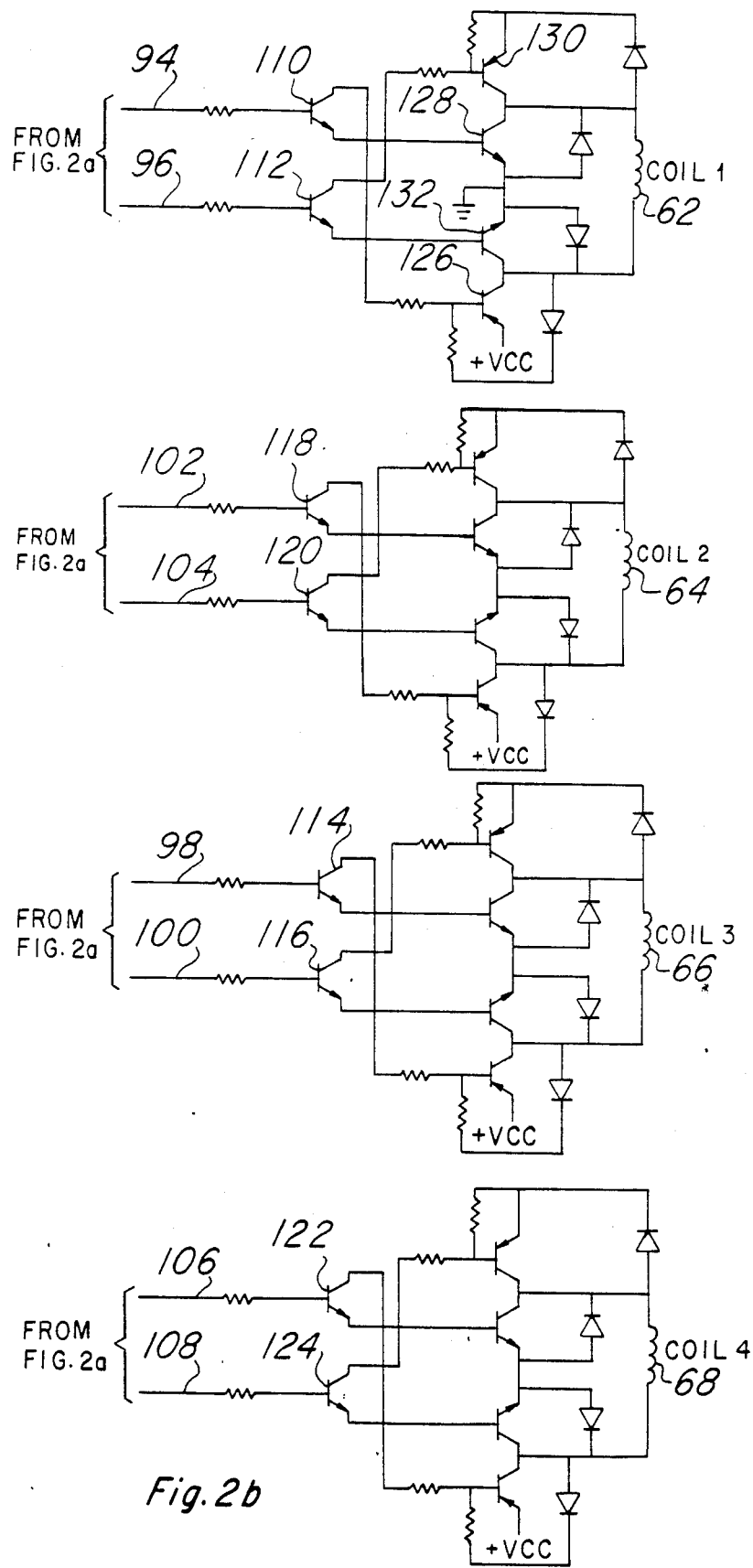

Referring now to FIGS. 2a and 2b, the interlace control circuit includes a timing clock 70 (FIG. 2a), a NAND gate 72 connected to the clock, a JK flip flop 74 connected to NAND gate 72 and a quad AND gate 76 connected to the flip flop 74 for supplying clocking pulses to a plurality of one shot multivibrators 78, 80, 82 and 84 as follows.

The quad AND gate 76 has terminal Vin connected to a source of power. In addition the following terminals of the gate 76 are connected to the following terminals of flip-flop 74: 4A to 1Q bar, 4B to 2Q, 3B to 2 and 1Q, 3A to 2Q, 1A to 2Q, 1B to 1Q, 2A to 2Q and 2B to 1Q bar. The following terminals of gate 76 are connected to other terminals of said gate: 4A to 2B, 4B to 3A, 3B to 1B, 3A to 4B and 1A to 2A. Also 4Y is coupled to 1B of one shot 78, 3Y is coupled to 1B of one shot 80, 1Y is coupled to 1B of one shot 84 and 2Y is coupled to 1B of one shot 82.

As each multivibrator is identical in structure only one need be described. Thus, referring to multivibrator 78 the $V_{cc}$, 1 CLR and 2 CLR input terminals are connected to the source of power and input terminals 2A, 1A and Ground are grounded. While output terminals 1R/C and 1 $C_{ext}$ are connected, respectively, to the arm of a potentiometer 86 and through a capacitor 88 across the arm of the potentiometer and one end of the potentiometer's resistor. The other end of the potentiometer's resistor is connected to the source of power. Output terminals 2R/C and $2C_{ext}$ of multivibrator 78 are similarly connected via potentiometer 90 and capacitor 92 to the source of power.

Thus connected, the 1 R/C and $1C_{ext}$ connection circuits fix the lengths of the pulse output of 1Qs to magnetize the corresponding cores of the electromagnet and the 2R/C and $2C_{ext}$ connection circuits fix the lengths of the pulse output of 2Qs to provide short negative pulses for demagnetizing quickly the corresponding cores of the electromagnet.

The 1Q and 2Q terminals of the one shot multivibrators 78, 80, 82 and 84 are connected by leads 94, 96, 98, 100, 102, 104, 106 and 108 to the bases of amplifiers 110, 112, 114, 116, 118, 122 and 124. Amplifier 110 has its collector connected to the base of transistor switch 126 and its emitter connected to the base of transistor 128.

While transistor 112 has its collector connected to the base of transistor switch 130 and its emitter connected to the base of transistor switch 132. Thus, when 1Q goes high transistor switch 126 turns ON and transistor switch 128 turns ON, and while 2Q is low transistor switch 130 is OFF and transistor 132 is off and current flows through the coil 62 in one direction to ground to magnetize its corresponding core. Then when 1Q goes low simultaneously therewith 2Q goes high to turn on transistor 130 and turn ON transistor 132. With 1Q low transistors 126 and 128 are off and the current in the coil 62 reverses itself to demagnetize the corresponding coil quickly. As the remaining multivibrators are similarly connected to the remaining coils they need not be described.

Figure 3:
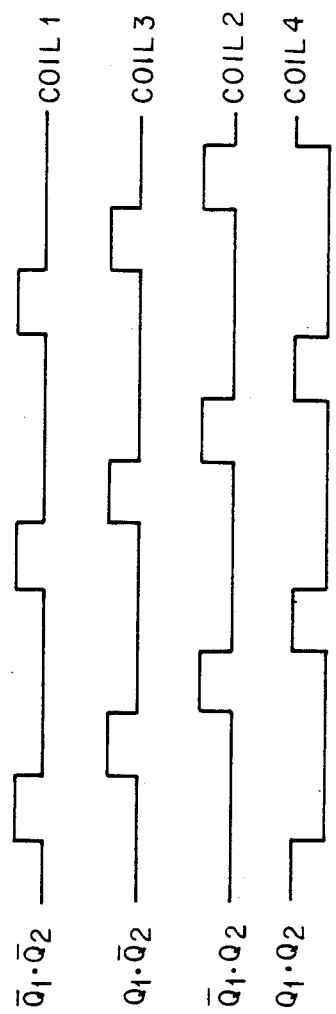
FIG. 3 is a timing diagram for the circuit of FIGS. 2a and 2b.
Figure 4:
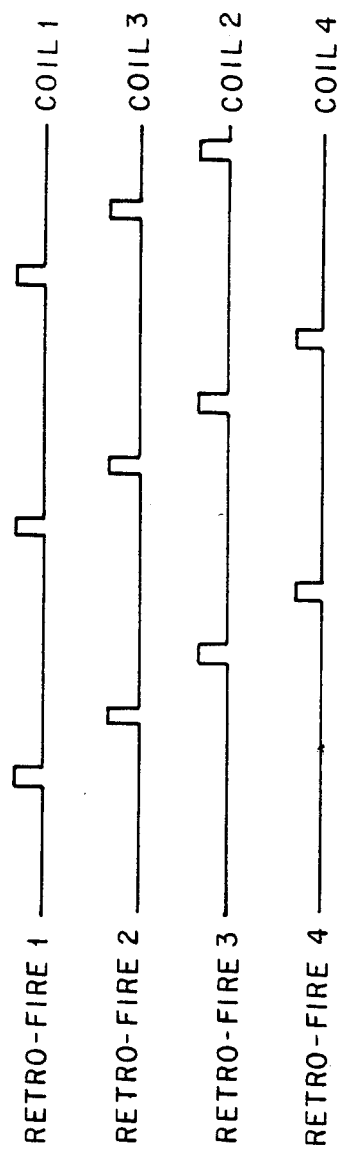
FIG. 4 is a timing diagram of retro-fire pulses for the circuit of FIGS. 2a and 2b.

The 1Q timing pulses are shown in FIG. 3 and the 2Q timing pulses are shown in FIG. 4. In operation the sequence for a single direction interlace scan is as follows: first, coil 62 is energized to draw the reed interlace mirror 12 into contact with surface segment 30, secondly, coil 66 is energized to rotate the interlace mirror into contact with surface segment 34, thirdly, coil 64 is energized to rotate the interlace mirror back to surface segment 32; and finally, coil 68 is energized to rotate the interlace mirror to surface segment 36. Then coil 62 is energized for fly back to surface 30 and the cycle repeated. It will be appreciated by those skilled in the art that the distance the interlace mirror travels is greatest between cycles when it travels from surface segment 36 back to surface segment 30. In a two directional interlace scan, the difference in fly time is eliminated as coil 64 is energized after coil 68 to rotate the interlace mirror to surface 32, followed in sequence by the energization of cols 66 and 62 to rotate the interlace mirror to surfaces 34 and 30, respectively. Thus, in the two direction interlace the distance traveled is always the same.

Although only a single embodiment of this invention has been described, it will be apparent to a person skilled in the art that various modifications to the details of construction shown and described may be made without departing from the scope of this invention.

What is claimed is:

1. A multiple position interlacer comprising:
   (a) an interlace mirror including magnetic material;
   (b) a support body of magnetic material for supporting the interlace mirror, said support body including a surface having a plurality of surface segments sloping downwardly from a central ridge formed by adjacent surface edges, each surface segment having a sloping, flat surface forming a facet of a preselected interlace angle, a plurality of non-magnetic bars for dividing the support body into a plurality of magnetic cores beneath the facets and a plurality of coils mounted within the plurality of magnetic cores; and
   (c) an electrical control circuit means operatively connected to the plurality of coils for selectively energizing the coils to move the interlace mirror through preselected angles whereby a plurality of interlaced lines is formed of the energy impinging on the interlace mirror.

2. A multiple position interlacer according to claim 1, wherein the control circuit means includes a signal generating means for sequentially producing first signals of a first polarity for selectively energizing the coils of the body support for selectively magnetizing the cores thereof and second signals of an opposite polarity, a second signal being produced at the end of each first signal for expediting the demagnetization of the corresponding core.

3. A multiple position interlacer according to claim 1 further including a second facet on each side of said central ridge having a ridge between each said second facet and the other facet on the side of the central ridge thereof and a separate one of said coils associated with each of said facets.

4. A multiple position interlacer according to claim 2 further including a second facet on each side of said central ridge having a ridge between each said second facet and the other facet on the side of the central ridge thereof and a separate one of said coils associated with each of said facets.

5. A multiple position interlacer comprising:
   (a) an interlace mirror including magnetic material;
   (b) a support body of magnetic material for supporting the interlace mirror, said support body including a surface having a plurality of surface segments sloping downwardly from a central ridge formed by adjacent surface edges, each surface segment having a sloping, flat surface forming a facet of a preselected interlace angle, a plurality of non-magnetic bars for dividing the support body into a plurality of magnetic cords beneath the facets and a plurality of coils mounted within the plurality of magnetic cores; and
   (c) an electrical control circuit means operatively connected to the plurality of coils for selectively energizing the coils to move the interlace mirror through preselected angles whereby a plurality of interlaced lines is formed of the energy impinging on the interlace mirror, wherein the control circuit means includes a signal generating means for sequentially producing first signals of a first polarity for selectively energizing the coils of the body support for selectively magnetizing the cores thereof and second signals of an opposite polarity, a second signal being produced at the end of each first signal for expediting the demagnetization of the corresponding core, wherein the signal generating means includes a clock means, logic circuitry operatively connected to the clock means for producing a plurality of control signals, and a switching means operatively connected to the logic control means for sequentially introducing current flowing in a first direction for energizing the coils a preselected time and then sequentially introducing current flowing in a second direction in the coils for deenergizing the coils a preselected time prior to turn off whereby the coils first energize the cores in a first direction followed by energization in a second direction prior to cutoff for expediting demagnetization of the coils.

6. A multiple position interlacer according to claim 5 wherein the switching means comprises a plurality of solid state switches operatively connected to the logic circuitry.

7. A multiple position interlacer according to claim 6 wherein the logic circuitry includes a flip flop circuit connected to the clock means for producing a plurality of control signals, a plurality of AND gates operatively connected to the flip flop circuit for selectively generating a plurality of logic high and low signals, a plurality of one shot multivibrator circuits operatively connected to the plurality of AND gates for outputting simultaneously a plurality of high/low pulses of a first preselected length and then a plurality of low/high signals of a second preselected length, a plurality of solid state transistors operatively connected to the plurality of one shot multivibrator circuits for receiving the high/low and low/high signals, respectively, and a plurality of solid state switches operatively connected to the plurality of solid state transistors for selectively switching the high/low and low/high signals to the plurality of coils of the support member.

* * * * *